United States Patent
Lin et al.

[11] Patent Number: 5,944,578
[45] Date of Patent: Aug. 31, 1999

[54] BRA LINING WITH MASSAGE FUNCTION

[76] Inventors: Hsien-Yih Lin, Suit 16, 6th Floor, No. 183 Hsiao-Ya Road, Chia-I; Jung-Chung Hsien, Suit 3, 4th Floor, No. 12, Lane 316, Chung-Shan South Road, Yung Kang, Tainan Hsien, both of Taiwan

[21] Appl. No.: 09/121,730
[22] Filed: Jul. 24, 1998

[30] Foreign Application Priority Data

Oct. 4, 1997 [TW] Taiwan ................................ 86216963

[51] Int. Cl.⁶ .................................................... A41C 3/10
[52] U.S. Cl. .................................. 450/57; 2/267; 450/30
[58] Field of Search .................................. 450/30, 31, 32, 450/53, 54, 55, 56, 57; 2/267, 268, 2, 455, 456, 459, 460, 461, 462, 463, 464, 465, 466, 467

[56] References Cited

U.S. PATENT DOCUMENTS

| | | | |
|---|---|---|---|
| 3,304,558 | 2/1967 | Mann | 450/57 |
| 4,419,283 | 12/1983 | Schneider | 252/600 |
| 5,782,671 | 7/1998 | Suen et al. | 450/3 |
| 5,823,852 | 10/1998 | Chu | 450/38 |

*Primary Examiner*—Gloria Hale
*Attorney, Agent, or Firm*—Rosenberg, Klein & Bilker

[57] ABSTRACT

A bra lining is mounted in a bra and includes a sealed main body containing thick oil and a number of gold foils therein. The oil flows inside the main body to provide a massage effect, while the gold foils increase magnetic energy around the breast of the human body to activate the cells.

1 Claim, 2 Drawing Sheets

BRA LINING WITH MASSAGE FUNCTION

BACKGROUND OF THE INVENTION

1. Field of the Invention

The present invention relates to a bar lining with massage function.

2. Description of the Related Art

Bra is important to women. However, currently available bras only provide a supporting function for the breasts of female. The present invention is intended to provide a bra lining having a massage function.

SUMMARY OF THE INVENTION

A bra lining in accordance with the present invention is mounted in a bra and comprises a sealed main body containing thick oil and a plurality of gold foils therein. The thick oil may flow inside the main body and thus provides a massage effect. In addition, the gold foils may increase magnetic energy around the breast of the human body to activate the cells.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
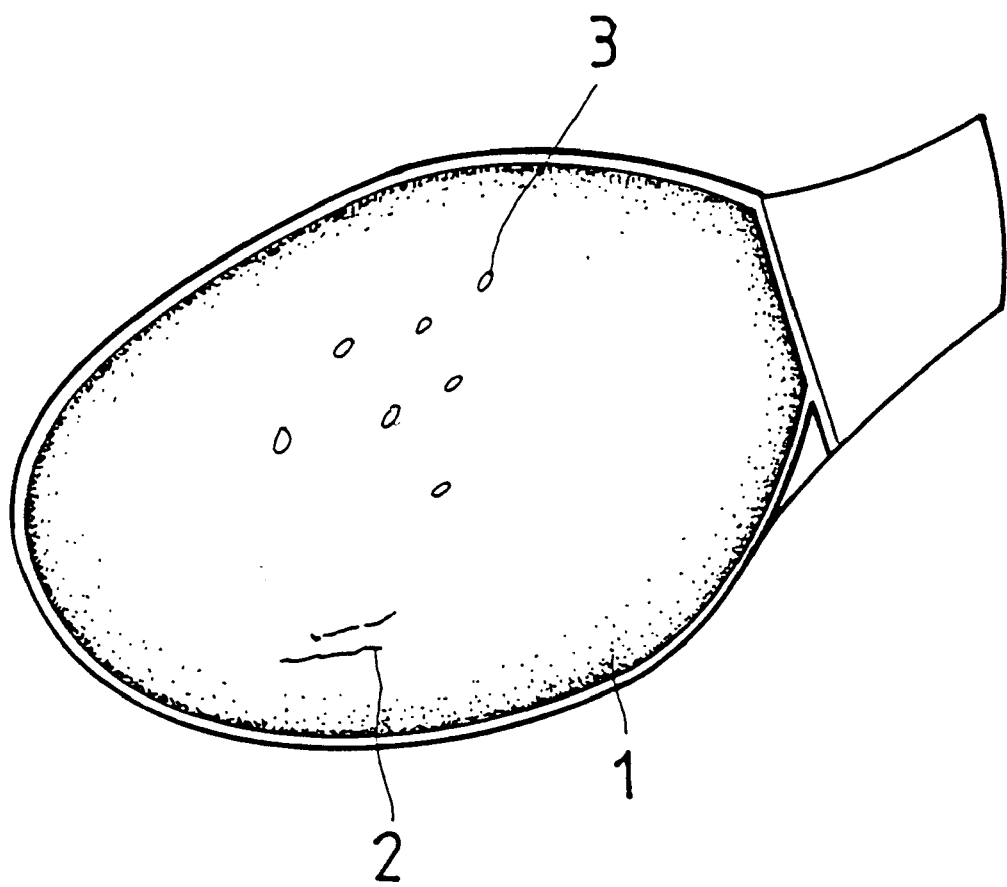
FIG. 1 is a perspective view of a bra lining in accordance with the present invention.

Referring to the FIG. 1, a bra lining in accordance with the present invention generally includes a main body 1 containing thick oil 2 and a plurality of gold foils 3 therein. The main body 1 is sealed to prevent leakage of the oil 2 and gold foils 3.

Figure 2:
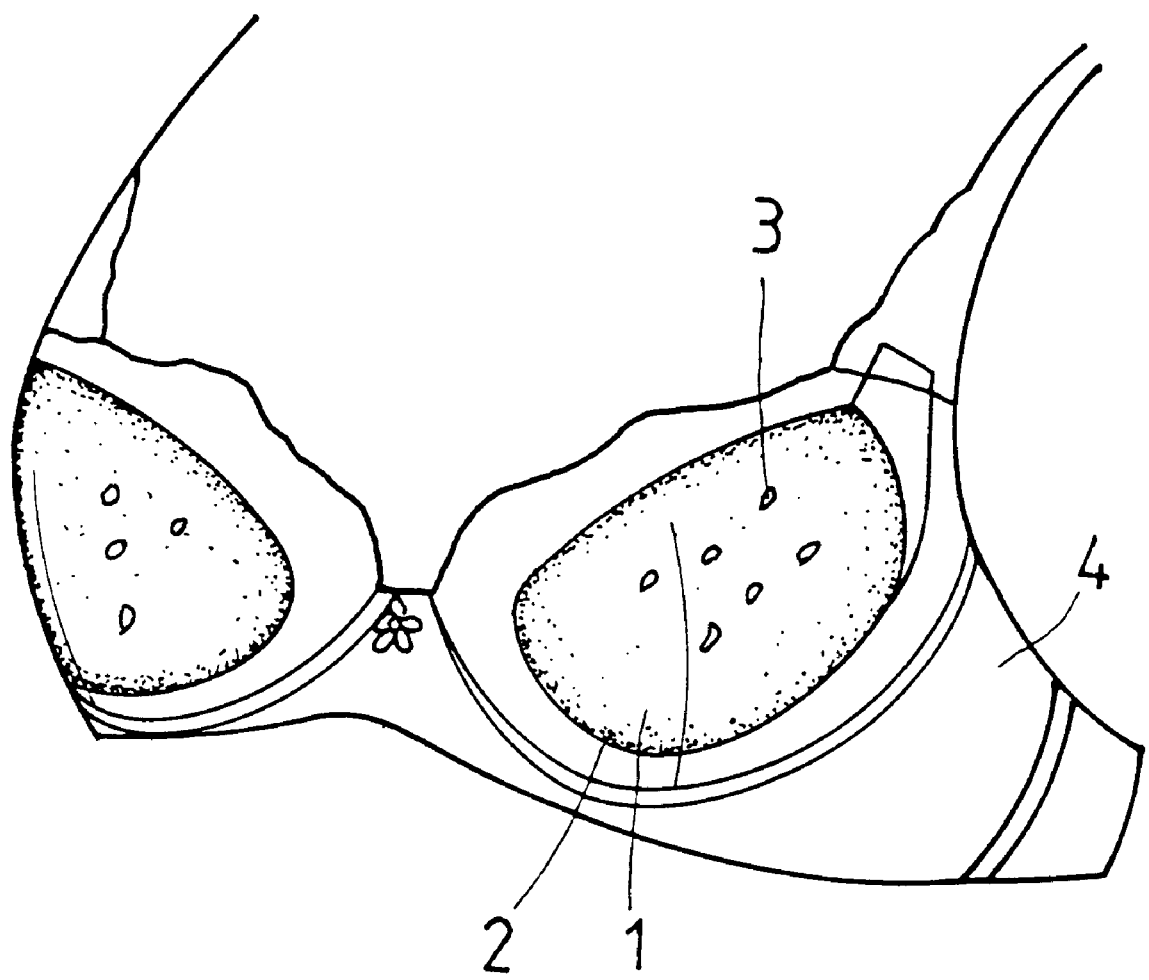
FIG. 2 is a perspective view of a bra equipped with the bra lining in accordance with the present invention.

In use, the bra lining is placed to an appropriate location in a bra 4, as shown in FIG. 2. It is appreciated that the thick oil 2 may flow inside the main body 1 and thus provides a massage effect. In addition, the gold foils 3 may increase magnetic energy around the breast of the human body to activate the cells. Thus, the user may be benefited.

Although the invention has been explained in relation to its preferred embodiment, it is to be understood that many other possible modifications and variations can be made without departing from the spirit and scope of the invention as hereinafter claimed.

What is claimed is:

1. A brassiere comprising:
   (a) a brassiere lining forming a liquid impermeable main body located within said brassiere;
   (b) a thick oil contained within said main body; and,
   (c) a plurality of gold foils contained within said main body.

* * * * *